United States Patent
Stahl et al.

(10) Patent No.: US 12,398,096 B2
(45) Date of Patent: *Aug. 26, 2025

(54) METHOD FOR PREPARING GUANIDINO ACETIC ACID

(71) Applicant: Evonik Operations GmbH, Essen (DE)

(72) Inventors: Timo Stahl, Limeshain (DE); Axel Ronneburg, Hanau (DE); Barbara Jäger, Mainhausen (DE); Philipp Roth, Hanau (DE)

(73) Assignee: Evonik Operations GmbH, Essen (DE)

( * ) Notice: Subject to any disclaimer, the term of this patent is extended or adjusted under 35 U.S.C. 154(b) by 310 days.

This patent is subject to a terminal disclaimer.

(21) Appl. No.: 18/043,268

(22) PCT Filed: Aug. 19, 2021

(86) PCT No.: PCT/EP2021/073004
§ 371 (c)(1),
(2) Date: Feb. 27, 2023

(87) PCT Pub. No.: WO2022/048913
PCT Pub. Date: Mar. 10, 2022

(65) Prior Publication Data
US 2024/0010611 A1    Jan. 11, 2024

(30) Foreign Application Priority Data
Sep. 1, 2020 (EP) .................................. 20193776

(51) Int. Cl.
*C07C 277/02* (2006.01)
*C07C 277/00* (2006.01)

(52) U.S. Cl.
CPC .......... *C07C 277/02* (2013.01); *C07C 277/00* (2013.01)

(58) Field of Classification Search
None
See application file for complete search history.

(56) References Cited

U.S. PATENT DOCUMENTS

| 10,844,009 | B2 * | 11/2020 | Stahl | B01D 61/44 |
| 11,795,142 | B2 * | 10/2023 | Stahl | C07C 277/00 |
| 2020/0207707 | A1 | 7/2020 | Stahl et al. | |

FOREIGN PATENT DOCUMENTS

| CN | 101462983 | 6/2009 |
| CN | 102329250 | 1/2012 |
| CN | 103193681 A | 7/2013 |
| CN | 204607896 U | 9/2015 |

(Continued)

OTHER PUBLICATIONS

Extended European Search Report dated Feb. 26, 2021, in European Application No. 20193776.0, 10 pages.

(Continued)

*Primary Examiner* — Amy C Bonaparte
(74) *Attorney, Agent, or Firm* — Grüneberg and Myers PLLC

(57) ABSTRACT

A method for preparing guanidino acetic acid involves reacting cyanamide and glycine in an aqueous reaction mixture in the presence of a base. The ammonia content in the reaction mixture is controlled to be below 20 g/L, and the dicyandiatrade content in the reaction mixture is kept below 5 wt.-%.

16 Claims, 1 Drawing Sheet

(56) References Cited

FOREIGN PATENT DOCUMENTS

| | | |
|---|---|---|
| CN | 105503659 | 4/2016 |
| CN | 210885881 U | 6/2020 |
| CN | 111393330 A | 7/2020 |
| CN | 211099033 U | 7/2020 |
| EP | 3 677 329 | 7/2020 |

OTHER PUBLICATIONS

Humm et al., "Recombinant expression and isolation of human L-arginine:glycine amidinotransferase and identification of its active-site cysteine residue", Biochem. J., vol. 322, 1997, pp. 771-776.
International Search Report dated Nov. 30, 2021, in PCT/EP2021/073004, 6 pages.
M. Strecker, comptes rendus 1861, 52, 1212, cited in Ber. Chem. Ges. (now: Eur. J. Inorg. Chem.), 1908, 41, pp. 4385.
Written Opinion dated Nov. 30, 2021, in PCT/EP2021/073004, 10 pages.
U.S. Pat. No. 10,844,009, Nov. 24, 2020, 2020/0207707, Stahl et al.
Office Action issued in Chinese Patent Application No. 202180041009.5 on Nov. 11, 2024, 13 pages including English translation.

\* cited by examiner

FIG. 1: Fed Batch
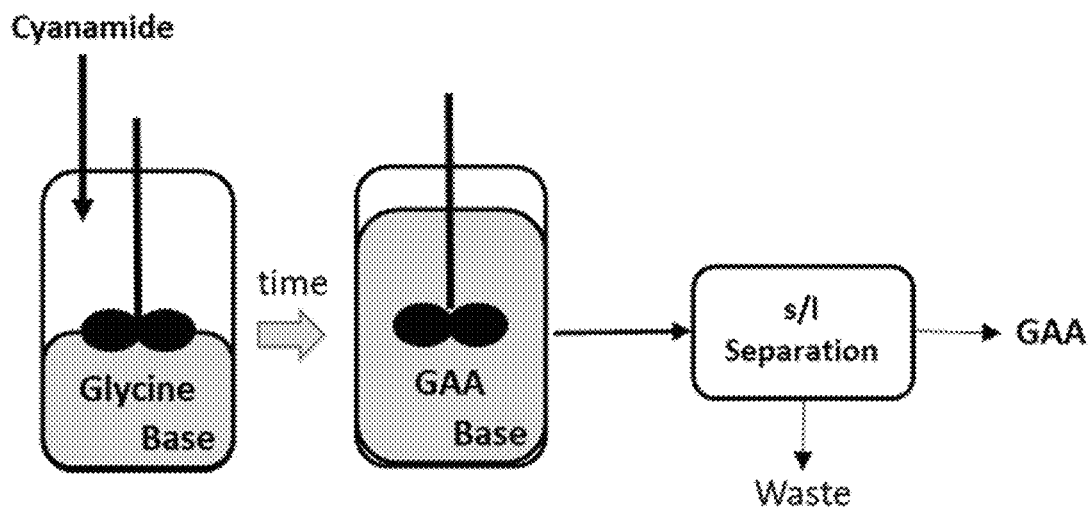
FIG. 2: Continuously operated reaction system
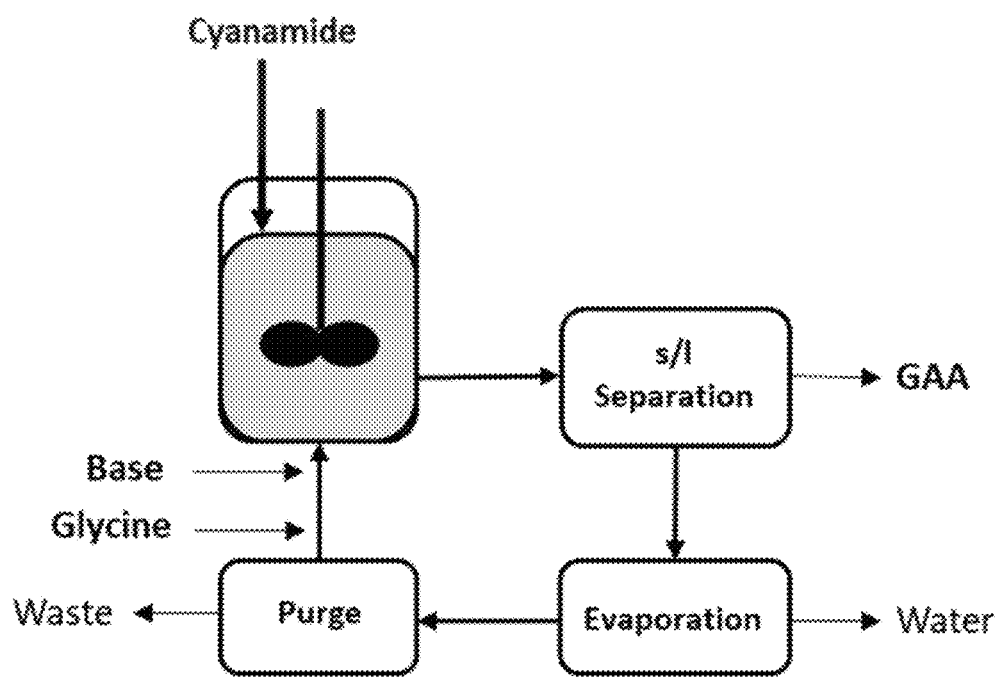

METHOD FOR PREPARING GUANIDINO ACETIC ACID

CROSS-REFERENCE TO RELATED APPLICATIONS

This application is the National Stage entry under § 371 of International Application No. PCT/EP2021/073004, filed on Aug. 19, 2021, and which claims the benefit of priority to European Application No. 20193776.0, filed on Sep. 1, 2020. The content of each of these applications is hereby incorporated by reference in its entirety.

BACKGROUND OF THE INVENTION

Field of the Invention

Guanidino acetic acid (GAA) is a colourless crystalline organic compound used as animal feed additive (WO 2005120246 A1/US 2011257075 A1). GAA is a natural precursor of creatine (e.g. Humm et al., Biochem. J. (1997) 322, 771-776). Therefore, the supplementation of GAA allows for an optimal supply of creatine in the organism.

Description of Related Art

The present invention concerns a method for preparing guanidino acetic acid (GAA) by reacting cyanamide with glycine in an aqueous reaction mixture in the presence of a base.

The production of GAA by adding cyanamide to glycine was first described in 1861 (M. Strecker, comptes rendus 1861, 52, 1212; cited in: Ber. Chem. Ges. (now: Eur. J. Inorg. Chem.) 1908, 41, 4385). A weakly alkaline aqueous ammonia solution was used as the reaction medium. More recent publications also include reaction conditions with sodium hydroxide solution or sodium carbonate as the base for setting the pH (e.g., CN 102329250 A and CN 101462983 A).

An alkaline environment (pH 8-10) is necessary for the production of GAA from cyanamide and glycine, but it is also the very same environment that can cause undesirable by-products, in particular dicyandiamide and melamine.

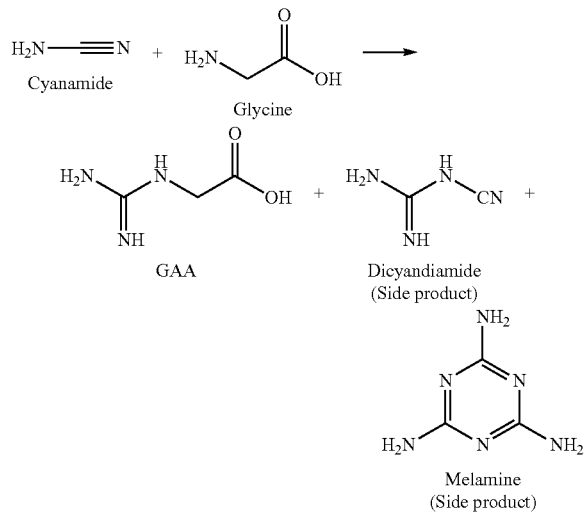

Two methods for GAA production from cyanamide and glycine are described in the literature (EP3677329A1 and CN 102329250 A) that come with challenges in this regard:

A) Adding a cyanamide solution to an alkaline glycine solution (fed batch; FIG. 1) B) Addition of glycine and cyanamide in a continuously operated reaction system with continuous recirculation of the glycine-containing mother liquor after product separation (FIG. 2).

A) Fed-Batch: Especially at reaction start, the setup is characterized by large glycine excess which suppresses side product formation. However, a large amount of base is necessary to adjust the pH value, because the glycine provided has an unfavourable pH buffering effect. During the reaction, however, glycine is consumed and the buffer effect diminishes, the pH rises too high and worsens the yield and selectivity. This undesired effect can be prevented by adding acid, but has not yet been described. The pH control with acid leads to an overall high rate of salt formation.

B) Continuously operated reaction system: For technical reasons, a continuous operation allows for having only a small excess of glycine in the reactor (typically: glycine:cyanamide=2:1), otherwise the circuit becomes too large. This results in poor selectivities. At the same time, by-products have to leave the cycle, otherwise there is a risk of accumulation. However, such a purge stream also removes large amounts of glycine, which are then lost.

Although the by-product dicyandiamide is formed in significantly higher quantities compared to melamine, melamine is the critical component, since its presence is regulated on a ppm scale, depending on the country. It is possible to purify the final GAA product through a washing step, but the high effort also results in high product and raw material losses in the washing water.

An alternative method for producing GAA is disclosed by CN105503659 A, GAA is formed by adding liquid ammonia to an aqueous solution of glycine to adjust the pH to 10, heating the solution up to 55° C. and adding a 50% aqueous cyanamide solution. Under these conditions it may be assumed that the ammonia content is kept under a threshold of 20 g/L. However, CN105503659 A is silent about the control of the dicyanamide content in this reaction, nor does it disclose anything about the control of melamine impurities obtained with this process.

SUMMARY OF THE INVENTION

It is therefore desirable to prevent or significantly reduce the formation of melamine in order to improve the economy of production of GAA from glycine and cyanamide, and at the same time, to increase the product quality.

This is achieved by a method for preparing guanidino acetic acid (GAA) from glycine and cyanamide, in which reaction conditions that facilitate melamine formation are avoided, in particular by a method for preparing guanidino acetic acid by reacting cyanamide and glycine in an aqueous reaction mixture in the presence of a base, wherein the ammonia content in the reaction mixture is controlled to be below 20 g/L and wherein the dicyandiamide content in the reaction mixture is kept below 5 wt.-%.

BRIEF DESCRIPTION OF THE DRAWINGS

FIG. 1 shows a Fed Batch.
FIG. 2 shows a continuously operated reaction system.

DETAILED DESCRIPTION OF THE INVENTION

Suitable bases for the method according to the present invention are e.g. the hydroxides, the bicarbonates, or the carbonates of potassium or sodium.

It is known that melamine can be formed from cyanamide, or through the reaction of cyanamide and dicyandiamide. However, both reactions usually require very high temperatures (see example 1) and cannot explain for significant melamine formation at low temperatures (see example 2). Since the typical reaction temperature for the preparation of GAA is below 100° C., another way of melamine formation is required to rationalize its observation. Contrary to the intuitive assumption that cyanamide is always required for melamine formation in aqueous solution below 100° C., we observed melamine formation in the absence of cyanamide (see example 3). In fact, the presence of dicyandiamide and ammonia facilitates the formation of traces of melamine as well (see examples 4 and 5). Which means according to the invention, that the absence of either dicyandiamide or ammonia allows for a GAA production with significantly reduced melamine content. According to the invention the content of dicyandiamide has to be below the solubility product which depends on the pH value and temperature.

Dicyandiamide formation is usually facilitated by either a low glycine:cyanamide ratio, or a too high pH-value during the GAA reaction. As described, a low glycine:cyanamide ratio is a typical technical challenge in continuous GAA processes, whereas a too high pH-value is often observed at the end of a fed batch process. As a third fact of dicyandiamide accumulation that applies to both GAA processes, recirculation of the mother liquor has a strong impact on actual dicyandiamide levels.

Slight ammonia formation during the GAA process is observed through all times. However, its formation is highly facilitated at too high pH-values, which is a challenge especially for the fed batch process. As another source, ammonia can also be used as the base in the GAA process, which directly implies high amounts of this chemical compound. In order to reduce the ammonia content or avoid its formation, ammonia should preferably not be used as a base, and the pH-value of the reaction should be carefully monitored and be kept below 10, which is of importance for the fed batch process, in particular. As another option, ammonia could also be stripped off the aqueous solution, which works for both process types.

Therefore, in the method according to the present invention the ammonia content may be controlled through at least one of the following measures (a) stripping off ammonia from the reaction mixture, which means in laboratory scale by fast stirring to enlarge the surface or in technical scale by stripping with an inert gas e.g. nitrogen or air
(b) adding an organic or inorganic acid in case the pH value raises to levels above pH=10

The pH of the reaction mixture may be measured by means of an electronic pH meter or by means of pH indicator paper.

The dicyandiamide content can be controlled by continuously adding cyanamide and glycine to the reaction mixture such that the molar ratio of glycine: cyanamide in the reaction mixture is 4:1 or higher as long as glycine is added to the reaction mixture. This may be achieved in that cyanamide is continuously reacted with an excess molar amount of glycine by simultaneously adding cyanamide and glycine to a pre-mixed aqueous solution comprising glycine and the base, wherein the rate of the simultaneous addition of cyanamide and glycine is adjusted such that the molar ratio of base to glycine within the reaction mixture is kept constant within a range between 0.1 and 0.4 during the entire period of the simultaneous addition of cyanamide and glycine.

This particular method in which the molar ratio of glycine: cyanamide in the reaction mixture is 4:1 or higher as long as glycine is added to the reaction mixture may be varied in that cyanamide is reacted with an overall equimolar amount of glycine and wherein in a subsequent step the remaining molar amount of cyanamide without glycine is continuously added to the glycine containing reaction mixture (resulting in an overall equimolar amount of cyanamide and glycine) under maintaining the pH of the reaction mixture within a range from about 8 to about 10 by adding an acid. During this subsequent step, ideally, the pH of the reaction mixture is kept within a range from about 8 to about 10 by adding an acid The acid added to the reaction mixture for pH control may be sulphurous acid, acetic acid, hydrochloric acid, carbonic acid, carbon dioxide, formic acid or phosphorous acid, preferably acetic and sulphurous acid or the amino acid glycine In the method according to the present invention the dicyandiamide content may be controlled by precipitating dicyandiamide from the reaction mixture. A suitable precipitating method, to which is explicitly referred, is for example disclosed in CN 211099033 U.

In one embodiment the GAA yield based on cyanamide is at least 15 mol-%, preferably at least 45 mol-%, more preferably at least 60 mol-%, even more preferred at least 70 mol-%, most preferred at least 90 mol-%.

Experimental Part

General Information

Suppliers:
  Glycine, p.a.: Merck KGaA, Darmstadt (Germany)
  Cyanamide 50% in $H_2O$: ABCR GmbH, Karlsruhe (Germany)
  Dicyandiamide: Alfa Aesar as part of Thermo Fischer Scientific, Kandel (Germany)
  Sodium hydroxide: Merck KGaA, Darmstadt (Germany)
  Ammonia 25% in $H_2O$: Merck KGaA, Darmstadt (Germany)

Devices:
  250 mL—three necked flask
  300 mL—pressure vessel

Analytics:
  GAA analysis via Agilent HPC
    Derivatization: none
    Column: Zorbax SB-Phenyl; column temperature: 30° C.
    UV-Detection at 200 nm
    Eluent: 1780 g $H_2O$+68 g ortho-phosphoric acid 85 wt.-% in $H_2O$
    Flow: 0.4 mL/min
    Retention time: 15.1 min Melamine analysis via Agilent HPC
  Derivatization: none
  Column: HiChrom Alltima 5μm C18; column temperature: 20° C.
  UV-Detection at 210 nm
  Eluent A: 1780 g $H_2O$+68 g ortho-phosphoric acid 85 wt.-% in $H_2O$
  Eluent B: Acetonitrile
  Time/Flow program:

| t [min] | Eluent A [%] | Eluent B [%] | Flow [mL/min] | Max. pressure [bar] |
|---|---|---|---|---|
| 0 | 95 | 5 | 0.1 | 400 |
| 2.0 | 95 | 5 | 0.5 | 400 |
| 2.1 | 95 | 5 | 0.2 | 400 |
| 14.0 | 95 | 5 | 0.2 | 400 |
| 14.5 | 95 | 5 | 0.5 | 400 |
| 20.0 | 95 | 5 | 0.5 | 400 |

Retention time: 18.0 min
The pH of the reaction mixture may be measured by means of an electronic pH meter or by means of pH indicator paper.

EXAMPLE 1

Dicyandiamide (8.4 g, 100 mmol) and aqueous cyanamide solution (8.4 g, 50 wt-%, 100 mmol) were mixed in a 300 mL-pressure vessel and subsequently heated to 120° C. for 4 h under stirring (pH value of the suspension=5). Melamine formation was determined by HPLC analysis of the formed reaction mixture.
Melamine outcome: 7.0 mmol

EXAMPLE 2

Dicyandiamide (8.4 g, 100 mmol) and aqueous sodium hydroxide solution (10 g, 0.004 wt-%, in water, 0.01 mmol, pH value of the suspension=9) were mixed in a 300 mL-pressure vessel and subsequently heated to 90° C. for 4 h under stirring. Melamine formation was determined by HPLC analysis of the formed reaction mixture.
Melamine outcome: 0.1 mmol

EXAMPLE 3

Dicyandiamide (8.4 g, 100 mmol) and aqueous sodium hydroxide solution (10 g, 0.004 wt-%, 0.01 mmol) were mixed in a 300 mL-pressure vessel (pH value of the suspension=10). The reaction mixture was heated to 90° C. for 4 h under stirring. Melamine formation was determined by HPLC analysis of the formed reaction mixture.
Melamine outcome: 5.0 mmol

EXAMPLE 4

Dicyandiamide (8.4 g, 100 mmol), water (45 g), sodium hydroxide (0.3 g, 8.5 mmol) and aqueous ammonia solution (5.3 g, 32 wt-%, 100 mmol) were mixed in a 300 mL-pressure vessel (pH value of the suspension=11). Aqueous cyanamide solution (8.4 g, 50 wt-%, 100 mmol) was added and the reaction mixture was heated to 90° C. for 4 h under stirring. Melamine formation was determined by HPLC analysis of the formed reaction mixture.
Melamine outcome: 4.6 mmol

EXAMPLE 5

Dicyandiamide (8.4 g, 100 mmol) and aqueous ammonia solution (5.3 g, 32 wt-%, 100 mmol) were mixed in a 300 mL-pressure vessel. Aqueous cyanamide solution (8.4 g, 50 wt-%, 100 mmol) was added and the reaction mixture was heated to 90° C. for 4 h under stirring. Melamine formation was determined by HPLC analysis of the formed reaction mixture.
Melamine outcome: 5.0 mmol

TABLE 1

Summary of the experiments 1 to 5-conditions for melamine formation

| | Input at reaction start | | | | | | Outcome |
|---|---|---|---|---|---|---|---|
| | Cyanamide | Dicyandiamide | | NaOH | $NH_3$ | | Temp | Melamine |
| Example | [mmol] | [mmol] | ([wt-%]) | [mmol] | [mmol] | pH | [° C.] | [mmol] |
| 1 | 100 | 100 | (50) | — | — | 5 | 120 | 7.0 |
| 2 | — | 100 | (46) | 1 | — | 9 | 90 | 0.1 |
| 3 | — | 100 | (46) | 10 | — | 10 | 90 | 0.1 |
| 4 | — | 100 | (12) | 1 | 100 | 11 | 90 | 4.6 |
| 5 | — | 100 | (38) | — | 100 | 11 | 80 | 5.0 |

EXAMPLE 6—GAA synthesis according to the invention but additionally at elevated dicyandiamide contents (sealed system)

Dicyandiamide (8.4 g, 100 mmol), water (50 g), sodium hydroxide (0.65 g, 16 mmol) and glycine (7.5 g, 100 mmol) were mixed in a 300 mL-pressure vessel (pH value of the suspension =9.5). 25 Aqueous cyanamide solution (8.4 g, 50 wt-%, 100 mmol) was added. The reaction mixture was heated to 90° C. for 4 h under stirring to ensure completion of the reaction to GAA. Both Melamine and GAA formation was determined by HPLC analysis of the formed suspension.
GAA yield based on cyanamide: 91%
Melamine outcome: 0.4 mmol EXAMPLE 7—GAA synthesis according to the invention but additionally at elevated dicyandiamide contents (open system)

Dicyandiamide (8.4 g, 100 mmol), water (50 g), sodium hydroxide (0.65 g, 16 mmol) and glycine (7.5 g, 100 mmol) were mixed in a 250 mL - three necked flask (pH value of the suspension =9.5). Aqueous cyanamide solution (8.4 g, 50 wt-%, 100 mmol) was added. The reaction mixture was heated to 90° C. for 4 h under stirring to ensure completion of the reaction to GAA. Fast stirring leads to an enlarged surface which means that the ammonia can easily escape from the reaction mixture. The ammonia was clearly noticeable in the gas phase in terms of smell. Both Melamine and GAA formation was determined by HPLC analysis of the formed suspension.
GAA yield based on cyanamide: 93%
Melamine outcome: 0.4 mmol EXAMPLE 8 —GAA synthesis at high dicyandiamide contents and at high pH values (sealed system)

Dicyandiamide (8.4 g, 100 mmol), water (50 g), sodium hydroxide (4.0 g, 100 mmol) and glycine (7.5 g, 100 mmol) were mixed in a 300 mL-pressure vessel (pH of the suspension=12). Aqueous cyanamide solution (8.4 g, 50 wt-%, 100 mmol) was added. The reaction mixture was heated to for 4 hours under stirring to ensure completion of the reaction to GAA. Both Melamine and GAA formation was determined by HPLC analysis of the formed suspension.
GAA yield based on cyanamide: 44%
Melamine outcome: 9.4 mmol EXAMPLE 9 —GAA synthesis at high dicyandiamide contents and at high pH values (open system)

Dicyandiamide (8.4 g, 100 mmol), water (50 g), sodium hydroxide (4.0 g, 100 mmol) and glycine (7.5 g, 100 mmol) were mixed in a 250 mL - three necked flask (pH of the suspension=12). Aqueous cyanamide solution (8.4 g, 50 wt-%, 100 mmol) was added. The reaction mixture was heated to 90° C. for 4 hours under stirring to ensure completion of the reaction to GAA. Both Melamine and GAA formation was determined by HPLC analysis of the formed suspension.
GAA yield based on cyanamide: 37%
Melamine outcome: 4.1 mmol EXAMPLE 10 —GAA synthesis at high pH values (sealed system)

Glycine (7.5 g, 100 mmol), water (58 g), and sodium hydroxide (4.0 g, 100 mmol) were mixed in a 300 mL-pressure vessel (pH of the suspension=12). Aqueous cyanamide solution (8.4 g, 50 wt-%, 100 mmol) was added. The reaction mixture was heated to 90° C. for 4 hours under stirring to ensure completion of the reaction to GAA. Both Melamine and GAA formation was determined by HPLC analysis of the formed suspension.
GAA yield based on cyanamide: 22%
Melamine outcome: 0.9 mmol Example 11 —GAA synthesis at high pH values (open system) Glycine (7.5 g, 100 mmol), water (58 g), and sodium hydroxide (4.0 g, 100 mmol) were mixed in a 250 mL—three necked flask (pH of the suspension=12). Aqueous cyanamide solution (8.4 g, 50 wt-%, 100 mmol) was added. The reaction mixture was heated to 90° C. for 4 hours under stirring to ensure completion of the reaction to GAA. Both Melamine and GAA formation was determined by HPLC analysis of the formed suspension.
GAA yield based on cyanamide: 17%
Melamine outcome: 0.8 mmol

TABLE 2

| | GAA synthesis performed for 4 h in open and in sealed pressure devices | | | | | | | | |
|---|---|---|---|---|---|---|---|---|---|
| | Input at reaction start | | | | | | | Outcome | |
| Example | Cyanamide [mmol] | Glycine [mmol] | Dicyandiamide [mmol] ([wt-%]) | NaOH [mmol] | $NH_3$ [mmol] | Temp [° C.] | System[1] | GAA [%][2] | Melamine [mmol] |
| 6 | 100 | 100 | 100 (11) | 15 | — | 90 | Sealed | 91% | 0.4 |
| 7 | 100 | 100 | 100 (11) | 15 | — | 90 | Open | 93% | 0.4 |
| 8 | 100 | 100 | 100 (11) | 100 | — | 90 | Sealed | 44% | 9.4 |
| 9 | 100 | 100 | 100 (11) | 100 | — | 90 | Open | 37% | 4.1 |
| 10 | 100 | 100 | 0 | 100 | — | 90 | Sealed | 22% | 0.9 |
| 11 | 100 | 100 | 0 | 100 | — | 90 | Open | 17% | 0.8 |

[1]"Sealed" means systems in which the ammonia formed cannot escape. The system corresponds to a real production plant, which is not a closed system, but which it is also difficult for ammonia to escape due to the large volumes. "Open" means an open, small system with a stir bar, where a "stripping" of ammonia can be simulated, since the escape of ammonia is simplified;
[2]GAA yield [mol-%] is based on cyanamide.

EXAMPLE 6-11: General Remarks

Examples 6 and 7 have been performed under conditions according to the invention but an equimolar amount of dicyanamide (100 mmol/11 weight %) has been added to the reaction mixture. These examples show that reactions under the conditions without ammonia and without ammonia-forming conditions (pH=9.5) even with dicyandiamide additionally added to the reaction mixtures still result in very low melamine concentrations.

Examples 8 and 9: The reactions under the conditions with ammonia and with ammonia-forming conditions (pH>10) and with dicyandiamide in the reaction mixture result in high melamine 20 concentrations.

Examples 10 and 11: The reactions under the conditions without ammonia and with ammonia-forming conditions (pH>10) and without dicyandiamide in the reaction mixture result in low melamine concentrations.

"Sealed" means systems in which the ammonia formed cannot escape. The system corresponds to a real production plant, which is not a closed system, but which it is also difficult for ammonia to escape due to the large volumes. Therefore, there are also higher ammonia concentration values here.

"Open" means an open, small system with a stir bar, where a "stripping" of ammonia can be simulated, since the escape of ammonia is simplified. In the experiments, even under conditions for high melamine contents, less melamine was actually found than in the closed apparatus.

EXAMPLE 12: Method for producing GAA according to the invention

Glycine (4.3 kg, 57 mol), water (11.4 kg), and sodium hydroxide (50% in water, 1,5 kg 18.9 mol) were mixed. An aqueous cyanamide solution (50.4% in water, 3,4 kg, 40.5 mol) was added with 18mL/min for 178 min. The reaction was performed at 90 ° C. for 5 hours under stirring to ensure completion of the reaction to GAA.

Fast stirring leads to an enlarged surface which means that the ammonia can easily escape from the reaction mixture. The ammonia was clearly noticeable in the gas phase in terms of smell. The ammonium concertation of the reaction mixture was tested via commercially available colorimetric test kid (Merck, Ammonium test for use with MQUANT®). The ammonia concentration was between 5 g/l and 8 g/l during the reaction.

GAA and dicyandiamide formation were determined by HPLC analysis of the formed suspension.
GAA yield based on cyanamide: 67%,
Dicyandiamide 1.8 wt-%

EXAMPLE 13: Method to produce GAA according to the invention with control of pH In a 50 L reaction device, cyanamide (50 wt-% in H2O, 4.5 kg, 54 mol, 1.0 equiv., 24 mL/min for 178 min) was added to a solution of glycine (5.8 kg, 77 mol, 1.4 equiv.) and sodium hydroxide (50 wt-% in H2O, 1.2 kg, 15 mol) in water (16 kg, glycine content of solution: 25 wt-%) at 82° C. under stirring. After stirring for another 2 h at 82° C. the GAA yield was determined by HPLC analysis of 30 the formed suspension.
pH value at reaction start: 9, pH value at reaction end: 10.
GAA yield: 88% (5.6 kg).
Dicyandiamide 1.8 wt-%

EXAMPLE 14: Method to produce GAA according to the invention by continuously adding cyanamide and glycine and pH control In a 50 L reaction device, both cyanamide (50 wt-% in H2O, 4.5 kg, 54 mol, 1.0 equiv., 24 mL/min for 178 min) and a solution of glycine (4.6 kg, 62 mol, 1.1 equiv.) in water (14 kg, glycine content of 30 solution: 25 wt-%, in total 107 mL/min for 178 min) were added to a solution of glycine (1.2 kg, 15 mol, 0.28 equiv.) and sodium hydroxide (50 wt-% in H2O, 0.30 kg, 3.8 mol) in water (3.2 kg, glycine content of solution: 25 wt-%) at 82° C. under stirring. After stirring for another 2 h at 82° C. the GAA yield was determined by HPLC analysis of the formed suspension. pH value at reaction start: 9.5, pH value at reaction end: 8.9
GAA yield: 89% (5.7 kg).
Dicyandiamide 3.6 wt-%

The invention claimed is:

1. A method for preparing guanidino acetic acid, the method comprising:
   reacting cyanamide and glycine in an aqueous reaction mixture in the presence of a base,
   wherein an ammonia content in the reaction mixture is controlled to be below 20 g/L, and wherein a dicyandiamide content in the reaction mixture is kept below 5 wt.-%, and
   wherein the dicyandiamide content is controlled by continuously adding the cyanamide and the glycine to the reaction mixture such that the molar ratio of glycine:cyanamide in the reaction mixture is 4:1 or higher, as long as the glycine is added to the reaction mixture.

2. The method of claim 1, wherein the ammonia content is controlled through at least one of the following measures:
   (a) stripping off ammonia from the reaction mixture; and
   (b) adding an organic or inorganic acid when the pH value of the reaction mixture raises to levels above pH=10.

3. The method of claim 1, wherein the cyanamide is continuously reacted with the excess molar amount of the glycine by simultaneously adding the cyanamide and the glycine to a pre-mixed aqueous solution comprising the glycine and the base, wherein the rate of the simultaneous addition of the cyanamide and the glycine is adjusted such that the molar ratio of base to glycine within the reaction mixture is kept constant within a range between 0.1:1 and 0.4:1, but can vary within said range, during an entire period of the simultaneous addition of the cyanamide and the glycine.

4. The method of claim 1, wherein the dicyandiamide content is controlled by precipitating dicyandiamide from the reaction mixture.

5. The method of claim 1, wherein the base comprises a hydroxide, bicarbonates, or carbonates of potassium or sodium.

6. The method of claim 2, comprising measure (a).

7. The method of claim 2, comprising measure (b).

8. The method of claim 2, comprising measures (a) and (b).

9. The method of claim 2, wherein the dicyandiamide content is controlled by precipitating dicyandiamide from the reaction mixture.

10. The method of claim 3, wherein the dicyandiamide content is controlled by precipitating dicyandiamide from the reaction mixture.

11. The method of claim 2, wherein the base comprises a hydroxide, bicarbonates, or carbonates of potassium or sodium.

12. The method of claim 3, wherein the base comprises a hydroxide, bicarbonates, or carbonates of potassium or sodium.

13. The method of claim 1, wherein the guanidino acetic acid yield based on cyanamide is at least 15 mol-%.

14. The method of claim 1, wherein the guanidino acetic acid yield based on cyanamide is at least 45 mol-%.

15. The method of claim 1, wherein the guanidino acetic acid yield based on cyanamide is at least 90 mol-%.

16. The method of claim 1, wherein the base is sodium hydroxide.

\* \* \* \* \*